United States Patent
Feuer et al.

(10) Patent No.: US 7,214,353 B2
(45) Date of Patent: May 8, 2007

(54) PEPTIDE OR PROTEIN-CAPTURING SURFACES FOR HIGH THROUGHPUT MALDI MASS SPECTROMETRY

(75) Inventors: Bernice I. Feuer, Berkeley Heights, NJ (US); Jinlin Peng, Painted Post, NY (US); Ma Sha, Cambridge, MA (US)

(73) Assignee: Corning Incorporated, Corning, NY (US)

( * ) Notice: Subject to any disclaimer, the term of this patent is extended or adjusted under 35 U.S.C. 154(b) by 342 days.

(21) Appl. No.: 10/232,346

(22) Filed: Aug. 30, 2002

(65) Prior Publication Data

US 2004/0043497 A1    Mar. 4, 2004

(51) Int. Cl.
    *B01D 11/02*    (2006.01)
(52) U.S. Cl. .................. 422/261; 436/84; 436/86; 436/173
(58) Field of Classification Search ............. None
    See application file for complete search history.

(56) References Cited

U.S. PATENT DOCUMENTS 5,777,324 A  *  7/1998  Hillenkamp ............... 250/288
5,969,350 A  *  10/1999 Kerley et al. ............. 250/287

FOREIGN PATENT DOCUMENTS

GB          2332273 A  *  6/1999

OTHER PUBLICATIONS

Paborsky et al. "A nickel chelate microtiter plate assay for six histidine-containing proteins", Anal. Biochem., 1996, v. 234, pp. 60-65.*

Brockman et al. "A desalting approach for MALDI-MS using on-probe hydrophobic self-assembled monolayers", Anal. Chem., 1997, v. 69, pp. 4716-4720.*

J.M. Passner et al., "Structure of a DNA-bound Ultrabithorax-Extradenticle homeodomain complex", Nature, vol. 397, Feb. 25, 1999, pp. 714-719.

S. Naaby-Hansen et al., "Proteomics—Post-Genomic Cartography to Understand Gene Function", TRENDS in Pharmacological Sciences, vol. 22, No. 7, Jul. 2001, pp. 376-384.

L. Anderson et al., "A comparison of selected mRNA and protein abundances in human liver", Electrophoresis, 1997, vol. 18, pp. 533-537.

S. Gygi et al., "Correlation Between Protein and mRNA Abundance in Yeast", Molecular and Cellular Biology, Mar. 1999, vol. 19, No. 3, pp. 1720-1730.

A. Dove, "Proteomics: translating genomics into products?", Nature Biotechnology, vol. 17, Mar. 1999, pp. 233-236.

A.M. Edwards et al., "Proteomics: New tools for a new era", Modern Drug Discovery, 2000, vol. 5, No. 7, pp. 35, 38, 41-42, 44.

A. Abbott, "A post-genomic challenge: learning to read patterns of protein synthesis", Nature, vol. 402, Dec. 16, 1999, pp. 715-720.

K.H. Lee, "Proteomics: a technology-driven and technology-limited discovery science", TRENDS in Biotechnology, vol. 19, No. 6, Jun. 2001, pp. 217-222.

(Continued)

*Primary Examiner*—Yelena G. Gakh
(74) *Attorney, Agent, or Firm*—Thomas R. Beall; Vincent T. Kung; Tina N. Thompson

(57) ABSTRACT

Methods and compositions useful for capturing proteins or peptides from a sample mixture and analyzing the captured proteins or peptides via high throughput electrospray ionization (ESI) or matrix-assisted laser desorption/ionization mass spectrometry (HT MALDI MS) are provided. The methods and compositions are useful in large scale, simultaneous analyses of proteins and peptides present in a cell(s), tissue(s), or biological fluid(s).

6 Claims, 6 Drawing Sheets

OTHER PUBLICATIONS

J.B. Fenn et al., "Electrospray Ionization for Mass Spectrometry of Large Biomolecules", Science, vol. 246, Oct. 6, 1989, pp. 64-71.

M. Karas et al., "Laser Desorption Ionization of Proteins with Molecular Masses Exceeding 10,000 Daltons", Anal. Chem., 1998, vol. 60, pp. 2299-2301.

J.A. Loo, "Bioanalytical Mass Spectrometry: Many Flavors to Choose", Bioconjugate Chem., vol. 6, 1995, pp. 644-665.

M. Barber et al., "Fast Atom Bombardment of Solids (F.A.B.): A New Ion Source for Mass Spectrometry", J.C.S. Chem. Comm., 1981, pp. 325-327.

R. Aebersold et al., "Mass Spectrometry in Proteomics", Chem. Rev., 2001, vol. 101, pp. 269-295.

P. Chaurand et al., "Peptide and Protein Identification by Matrix-Assisted Laser Desorption Ionization (MALDI) and MALDI-Post-Source Decay Time-of-Flight Mass Spectrometry", J Am. Soc. Mass Spectrom., 1999, vol. 10, pp. 91-103.

J.A. Loo et al., "Tandem Mass Spectrometry of Very Large Molecules. 2. Dissociation of Multiply charged Proline-Containing Proteins from Electrospray Ionization", Anal. Chem., 1993, vol. 65, pp. 425-438.

H. Langen et al., "Two-dimensional map of the proteome of *Haernophilus influenzae*", Electrophoresis 2000, vol. 21, pp. 411-429.

M.G. Pluskal, "Microscale sample preparation", Nature Biotechnology, vol. 18, Jan. 2000, pp. 104-105.

R.C. Beavis et al., "Matrix-Assisted Laser Desorption Ionization Mass-Spectrometry of Proteins", Method in Enzymology, vol. 270, pp. 519-551.

M.Z. Wang et al., "A solid sample preparation method that reduces signal suppression effects in the MALDI analysis of peptides", Anal. Chem., 2001, vol. 73, pp. 625-631.

N. Zhang et al., "Two-layer sample preparation method for MALDI mass spectrometric analysis of protein and peptide samples containing sodium dodecyl sulfate", Analytical Chemistry, Jul. 1, 2001, vol. 73, No. 13, pp. 2968-2975.

A. Doucette et al., "Protein concentration and enzyme digestion on microbeads for MALDI-TOF peptide mass mapping of proteins from dilute solutions", Analytical Chemistry, vol. 72, No. 14, Jul. 15, 2000, pp. 3355-3362.

M. Esteban Warren et al., "On-probe solid-phase extraction/MALDI-MS using ion-pairing interactions for the cleanup of peptides and proteins", Analytical Chemistry, vol. 70, No. 18, Sep. 15, 1998, pp. 3757-3761.

M. Schürenberg et al., "Prestructured MALDI sample supports: sample washing and recrystallization", Bruker Daltonics 2001, pp. 1-3.

L.H. Sharpe et al., "Surface Energetics, Adhesion, and Adhesive Joints", Advances in Chemistry Series, pp. 189-201.

R.H. Hansen et al., "A new technique for preparing low surface energy polymers for adhesive bonding", Polymer Letters, vol. 4, pp. 203-209.

M.-S Sheu et al., "Immobilization of polyethylene oxide surfactants for non-fouling biomaterial surfaces using an argon glow discharge treatment", J. Adhesion Sci. Technol., vol. 7, No. 10, pp. 1065-1076 (1993).

J. Davies et al., Argon plasma treatment of polystyrene microtiter wells. Chemical and physical characterization by contact angle, ToF-SIMS, XPS and STM, Colloids and Surfaces A: Physiochem. Eng. Aspects, vol. 174, 2000, pp. 287-295.

R.B. Cole, "Electrospray Ionization Mass Spectrometry: Fundamentals, Instrumentation & Applications", Wiley, New York, 1997, Part 1, Chapters 1-4, pp. 1-174.

* cited by examiner

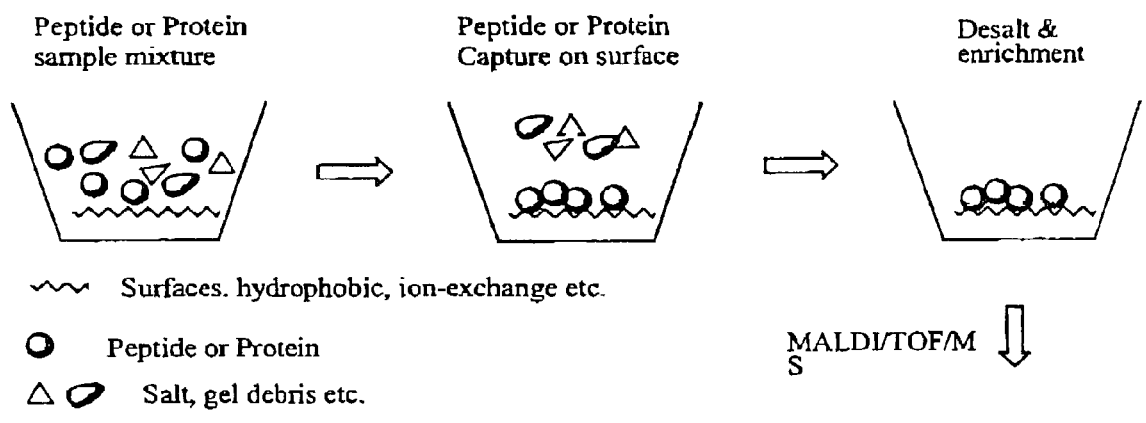
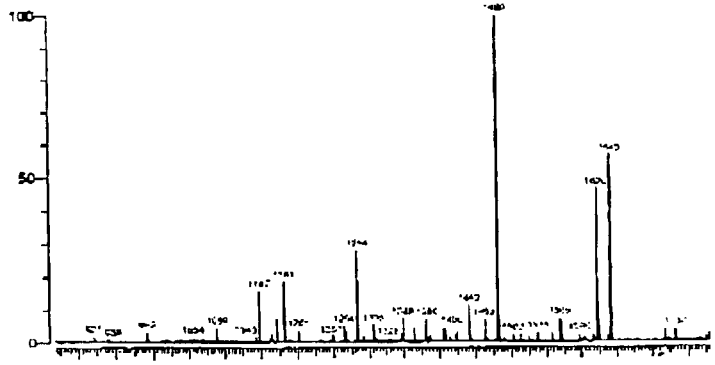
Figure 1

Figure 2A. Screening of different coating materials for protein capturing
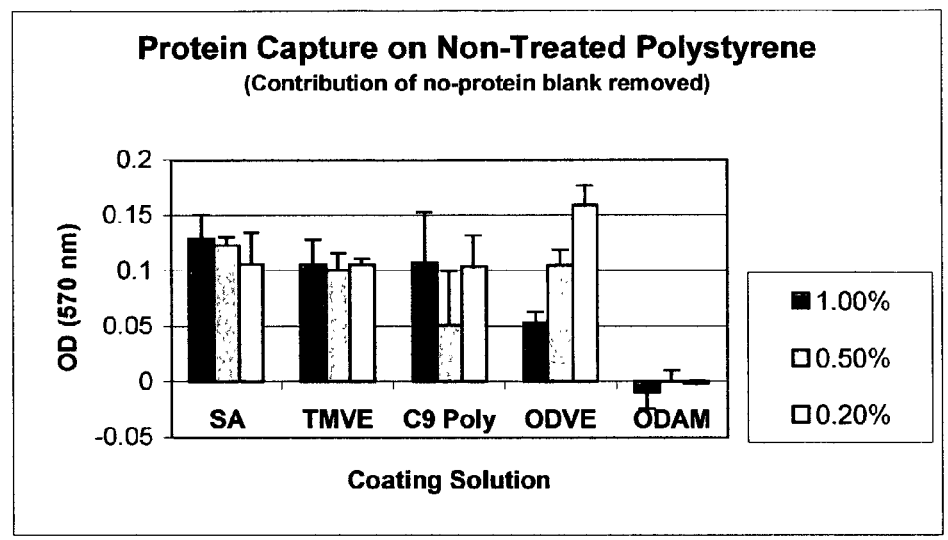
Figure. 2B. Impact of protein capture of ODVE coating by plasma treatment time
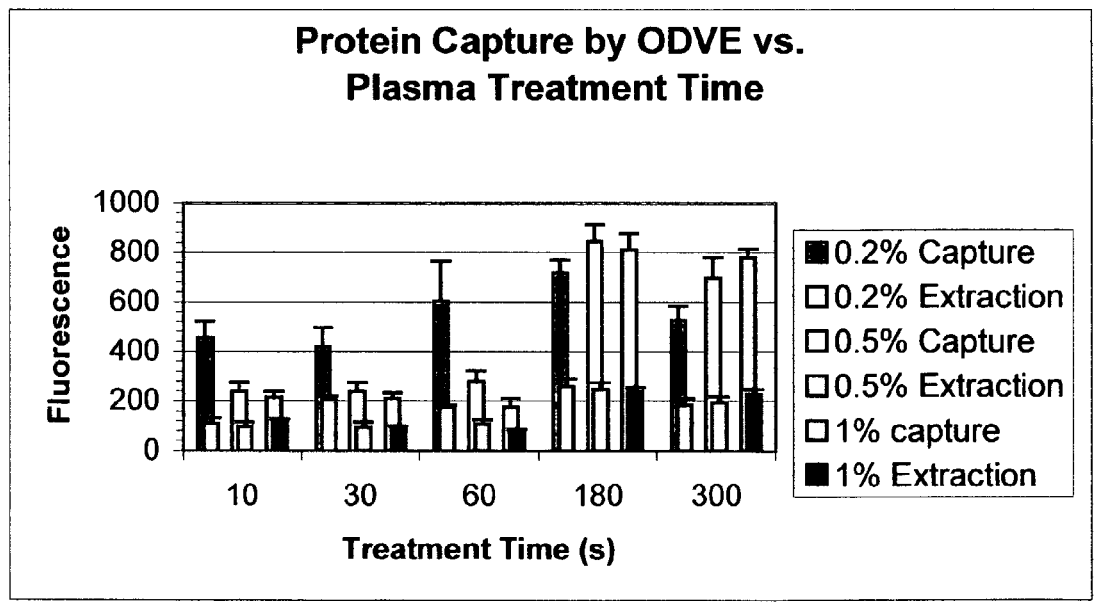

Figure 3. MALDI TOF spectra of ODVE coated plate vs. ZipTip™
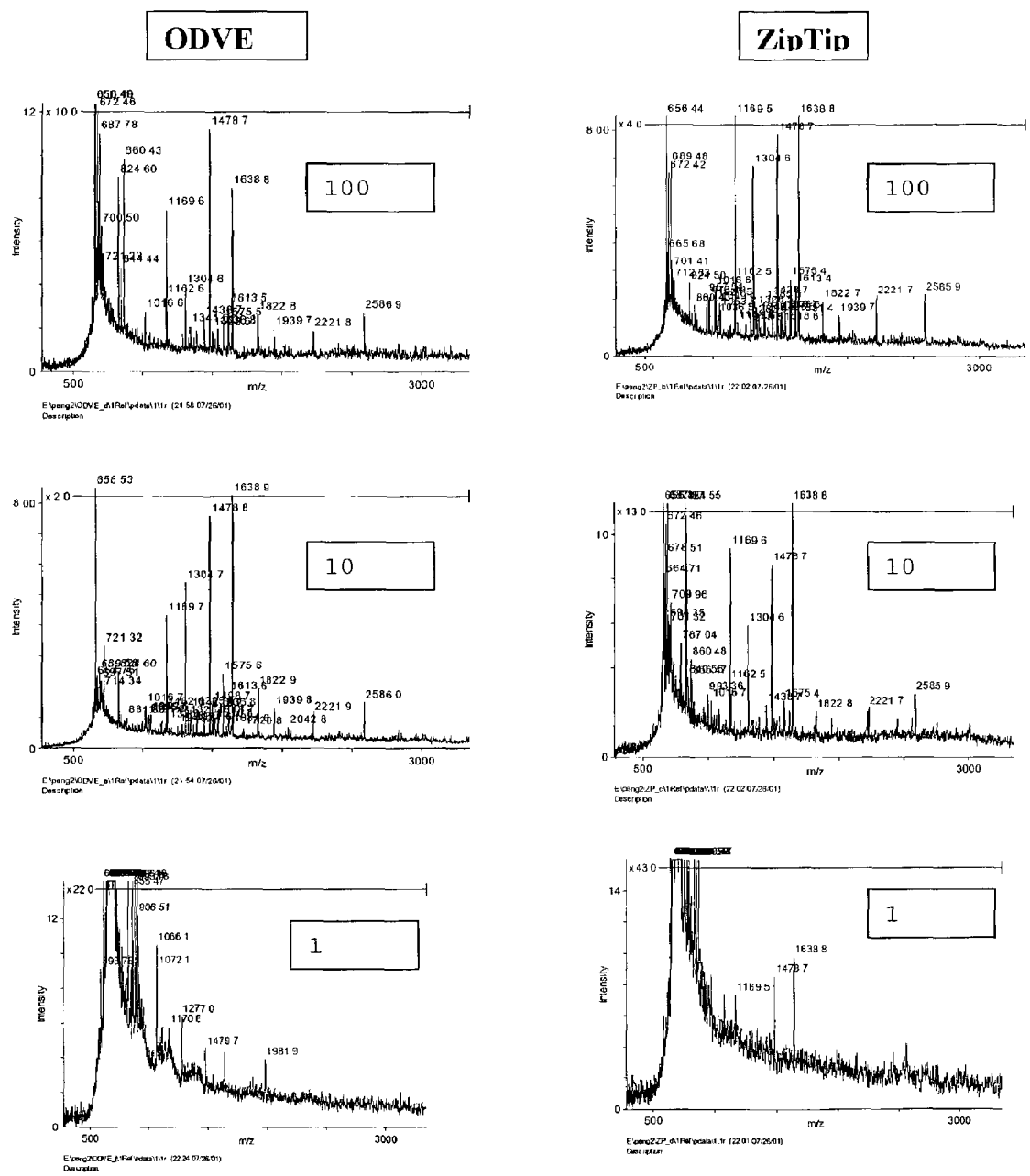

Figure 4. MALDI TOF MS spectra of Gold-deposited plate vs. ODAM-coated plate
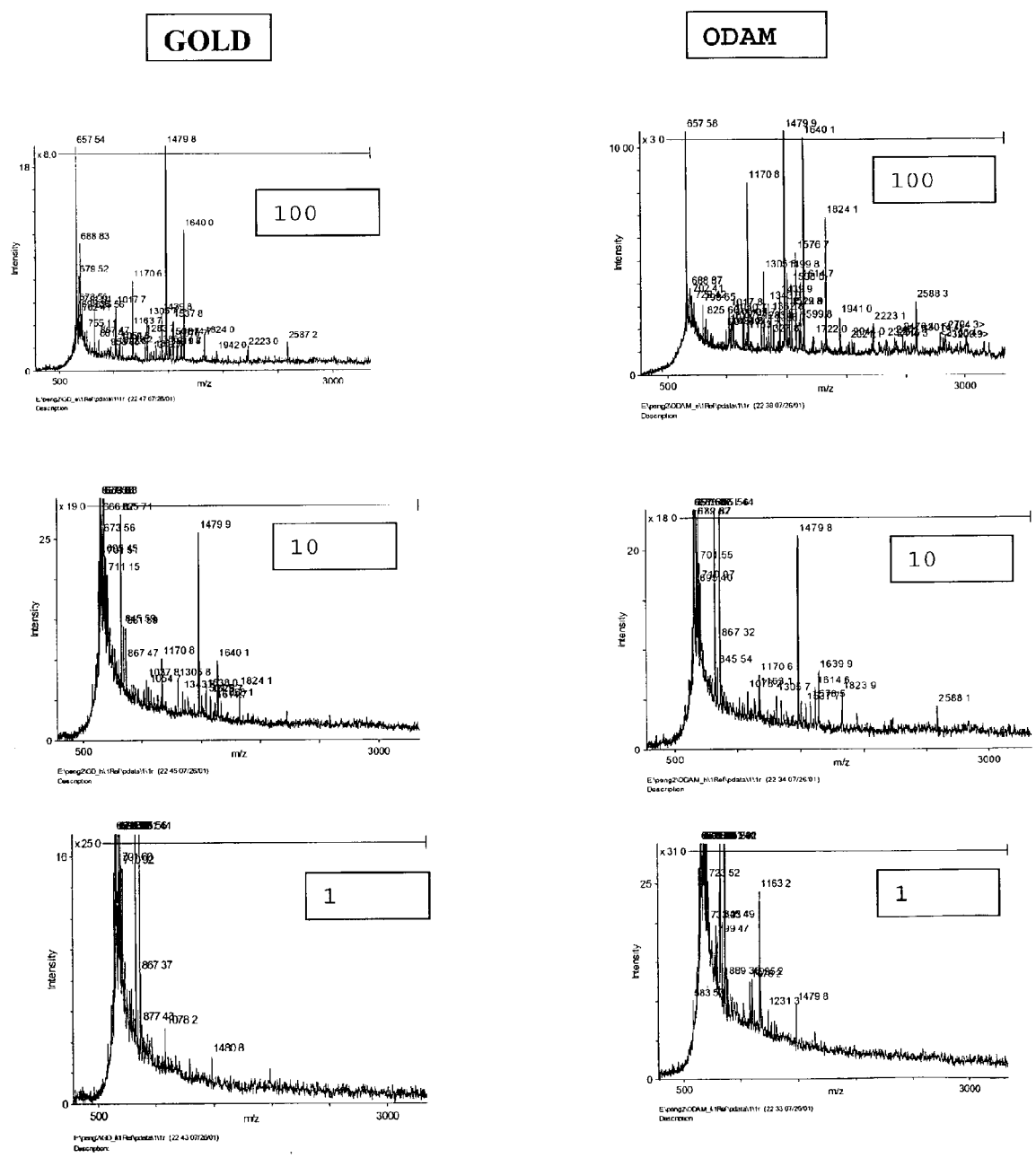

PEPTIDE OR PROTEIN-CAPTURING SURFACES FOR HIGH THROUGHPUT MALDI MASS SPECTROMETRY

FIELD OF THE INVENTION

The present invention relates to methods and compositions useful for capturing proteins or peptides from a sample mixture and analyzing the captured proteins or peptides via high throughput electrospray ionization (ESI) or matrix-assisted laser desorption/ionization mass spectrometry (HT MALDI MS). The subject methods and compositions are useful in large scale, simultaneous analyses of proteins and peptides present in a cell(s), tissue(s), or biological fluid(s).

BACKGROUND OF THE INVENTION

The inception of the now completed Human Genome Project has spurred an explosion in genomic research. DNA expression arrays, and other genomic tools were created to take advantage of the wealth of information promised, and currently provided by a completely sequenced human genome. As a result, genomics has come to dominate the biological landscape. Genomics, however, has its limits. Now more than ever, it is becoming clear that gene sequence alone cannot predict the fate or behavior of protein products. Though high throughput transcriptional profiling on DNA chips or microarrays can be used to determine when, where, and how much RNA is transcribed, there is rarely a relationship between RNA transcription and protein expression.[1,2,3] Post transcriptional modifications such as phosphorylation, and mRNA and peptide degradation can alter the function and concentration of a protein and are invisible to transcriptional profiling.

This gap between genomics and cellular behavior impedes elucidation of protein function as well as the identification of novel drug targets. Research in the post genomic era, then, will require a bridge between genomics and cellular behavior. Proteomics, which goal is to study the protein products of the genome, promises to be this bridge. By taking advantage of newly developed analytical tools, proteomics strives to study the dynamic, protein equivalent of the genome, the proteome. In so doing, proteomics would provide fundamental information on the molecular workings of the cell, as well the ability to observe the effect that specific diseases or drug treatments have on protein cascades.[4] Indeed, the potential ability of proteomics to provide information about proteins on a global scale is tremendous for pharmaceutical research, as over 75% of the predicted proteins in multicellular organisms have no known cellular function[5] and as many as 4,000 protein drug targets are predicted.[6]

Fundamental to proteomics are the abilities to both separate and identify proteins. Currently separation is achieved via several methods, the most popular being two dimensional gel electrophoresis (2-DE).[7] Separation by 2-DE is on the basis of charge (isoelectric focusing) and size (PAGE). Gels are stained by a variety of methods, including Coomassie blue stain, silver stain, fluorescent dyes, and radio labels. Once the gel is stained, proteins are easily located and excised from the gel. Currently, the most effective method for protein identification is by mass spectrometry (MS). The sensitivity of mass spectrometry, coupled with recently developed ionization methods, allows for accurate protein characterization and identification. Indeed, advancements in mass spectrometry are responsible for the growth of proteomics as a field.

The now inseparable relationship between mass spectrometry and proteomics can be traced to two technological breakthroughs in the late 1980's: electrospray ionization (ESI) and matrix-assisted laser desorption/ionization (MALDI).[8,9,10] In contrast to previous ionization methods, both ESI and MALDI are "soft" ionization methods, capable of generating ions from proteins and peptides without significant fragmentation. So soft are ESI and MALDI as ionization methods, that under certain conditions even non-covalent interactions are undisturbed, allowing for the analysis of large multi-protein complexes.[11] ESI is easily coupled to liquid phase chromatographic and electrophoric techniques, a quality for which the method quickly gained popularity. Due to this, and the method's tendency to produce multiple charged ions allowing detection outside the nominal m/z range of simple instruments, ESI soon became the method of choice for analysis of proteins in the liquid phase.[12,13]

Ions produced via MALDI are, in contrast, largely singly charged, providing mass spectra that are easily interpreted. Furthermore, the time-of flight (TOF) mass analyzer to which MALDI is most often coupled is robust, simple, sensitive, and capable of detecting proteins as large as 100,000 mass units (amu).[14,15] Both methods are now established as state of the art analytical tools in proteomics, finding applications in protein identification by mass mapping, and single peptide fragmentation, as well as the identification and characterization of post-translation modifications such as protein phosphorylation.[13] Perhaps the most popular of these applications is protein identification by mass mapping, in which proteins, once separated by 2-DE or HPLC, are digested by a sequence-specific proteolytic enzyme such as trypsin. Upon digestion by such an enzyme, a specific protein will produce a unique set of polypeptide sequences, which upon detection and analysis by MS, yields a polypeptide mass-map. This mass-map, which is unique, can be used to identify the protein. Peptide mass-mapping has been used in the proteomic analysis of *Haemophilus influenzae* as well as several strains of yeast used in the brewing industry.[16] Mass spectrometry is also used for protein sequencing, replacing Edman sequencing. Mass spectrometry allows for the analysis of subfemtomole quantities and is not restricted by N-terminal modifications, both problems associated with the Edman-based method.[17]

Neither ESI nor MALDI, however, are without limitations. Due to the attomolar sensitivity of both ESI and MALDI, and the small volume of MS samples, cleanliness of biological samples is perhaps the greatest limitation for proteomic MS.[18,19] This limitation is particularly noticeable in proteomics as protein samples obtained from 2-DE gel digestion contain salts, ionic detergents and involatile solvents that can greatly reduce signal intensity and resolving power.[20] The importance of sample cleaning and preparation is in fact so great that the literature abounds with novel sample prep protocols, particularly for the more popular MALDI method.[21,22,23]

Furthermore, the emergence of products specifically targeted at sample preparation for proteomic MS highlights the significance of this step. Millipore (Bedford, Mass.) has introduced the ZipTiP™, a 10 μl pipette tip packed with a polymer stabilized expanded bed (PSEB) of C18 reverse phase chromatographic media. When a protein or peptide sample is introduced into the pipette, peptides are captured by the C18 media via hydrobohic interactions. The sample can then be washed of impurities and subsequently eluted.[19] Sample cleaning with ZipTiP™ technology has been shown to significantly improve the signal-to noise ratio of peptide mass maps obtained from MALDI-TOF.[22]

Sample cleaning has also been achieved by assembling reverse-phase media directly onto the MALDI probe. A stainless steel MALDI probe is coated with gold, and then self-assembled monolayers (SAMs) are created by taking advantage of gold-thiol chemistry. At present, both C18 and ionic reverse phase media have been created.[23,24] Although both of these methods achieve sample cleaning and improve spectrum quality, they nonetheless fail to do so in high throughput fashion. Proteomics is a high throughput field and the need to individually purify and analyze samples with MS is severely limiting.[7] With this in mind, Bruker (Bremen, Germany) has designed the Anchor Chip, a MALDI target with 384 individual hydrophilic anchors. The Anchor Chip is stainless steel with a hydrohobic coating that allows for protein and peptide capture. Samples are spotted with a water insoluble matrix such as α-cyano 4-hydroxycinnamic acid (HCCA), and then washed. Samples are then re-dissolved and allowed to crystallize, whereupon they shrink to the hydrophilic anchor.[25] Despite allowing for high throughput in sample preparation and MS analysis, the anchor chip is cost prohibitive, and requires stringent washing prior to re-use. Furthermore, the presence of 384 liquid targets on a flat surface increases the possibility of cross-contamination.

In order to eliminate the bottle-neck of proteomic sample preparation, a high throughput tool is required. Ideally, this tool should be both inexpensive and disposable. Most importantly, the tool should reduce sample cross-contamination. The present invention overcomes problems in the art by providing such a tool.

SUMMARY OF THE INVENTION

The present invention provides compositions and methods useful in performing high throughput analysis of multiple protein and/or peptide samples. The compositions comprise a solid support having a plurality of compartments, wherein one or more of the compartments has a specific affinity layer attached thereto for capture of the peptides or proteins present in the samples. Preferably, more than one of the compartments has a specific affinity layer attached thereto. Even more preferably, all or almost all of the compartments have a specific affinity layer attached thereto.

The solid support may be comprised of any material as long as a specific affinity layer for capturing peptides or proteins may be attached thereto. Preferably, the solid support is comprised of a polymer such as polypropylene, cyclic olefin copolymer, polyethylene, polymethyl methacrylate, polyvinyl chloride, polymethyl pentene, polycarbonate, polysulfone, polystyrene copolymer, poly(styrene-co-maleic anhydride, polypropylene copolymer, fluoropolymer, or polyamide.

Conveniently, many readily available materials may be used in configuring the solid supports of the present invention. Examples include dishes, slides, strips or plates. Preferably, microwell plates or microtiter dishes are used.

Many different materials may be used as the specific affinity layer. Examples include hydrophobic surface layers, ionic surface layers, or metal chelating surface layers. Preferably, a hydrophobic surface layer is used. Even more preferably, the hydrophobic surface layer may comprise a long chain aliphatic, such as octadecyl vinyl ether (ODVE), octadecyl amine (ODAM), tri(ethylene glycol)-methyl-vinyl-ether (TMVE), stearyl alcohol (SA), nonylphenoxypoly (ethyleneoxy)ethyl-methacrylate (C9 poly), or stearyloxy-polyethyleneoxy-ethyl-methacrylate (SPMA). Specific species, such as octadecyl vinyl ether (ODVE) or octadecyl amine (ODAM), may be more preferred.

Various combinations of specific affinity layers and other surfaces may be used in the subject solid supports. For example, a specific affinity layer may be attached to a first portion of the one or more compartments and a non-binding surface may be located in a second portion of the one or more compartments. Alternatively, the one or more compartments having a specific affinity layer attached thereto may further have a hydrophilic area devoid of and surrounded by the specific affinity layer.

In still another embodiment, the solid support may have a specific affinity layer attached to a first portion of the one or more compartments, wherein the first portion of the one or more compartments comprises a hydrophilic area devoid of and surrounded by the specific affinity layer attached thereto and may further have the one or more compartments comprise a non-binding surface located in a second portion thereof.

The present invention also provides a method of performing high throughput analysis of multiple samples, each of said samples comprising a mixture of peptides or proteins. The methods employ use of a subject solid support. An example of such a method comprises the steps of:

(a) providing a solid support comprising a plurality of separate compartments, wherein one or more of the compartments has a specific affinity layer attached thereto for capture of the peptides or proteins present in the samples;

(b) applying each of said samples or an aliquot thereof, to a separate compartment having the specific affinity layer attached thereto;

(c) washing the peptides or proteins which have been captured by the specific affinity layer, and (d) performing high throughput electrospray ionization (ESI) or matrix-assisted laser desorption/ionization (MALDI) mass spectrometry analysis on the captured peptides or proteins.

BRIEF DESCRIPTION OF THE DRAWINGS

FIG. 1 depicts in a schematic the major steps of the present invention. A sample comprising a mixture of peptides or proteins is added to a separate compartment on or in a solid support having a specific affinity layer attached thereto. The specific affinity layer captures the peptides or proteins in the sample. The captured proteins are then washed and may be analyzed via MALDI MS as represented by the MS spectrum.

FIG. 2A shows the results of protein capture on non-treated polystyrene.

FIG. 2B graphically depicts the degree of protein attachment at varying concentrations of ODVE on coated plates as a function of plasma treatment time.

FIGS. 3A–3C show an ODVE coated plate to which a BSA digest was applied and processed (FIGS. A–C showing different sample sizes).

FIGS. 4A–4F show a comparison of MALDI TOF spectra for a gold deposited plate (A–C showing different sample sizes) and an ODAM coated plate, both of which had a BSA digest applied and processed (A–C showing different sample sizes).

DETAILED DESCRIPTION OF THE INVENTION

Figure 5:
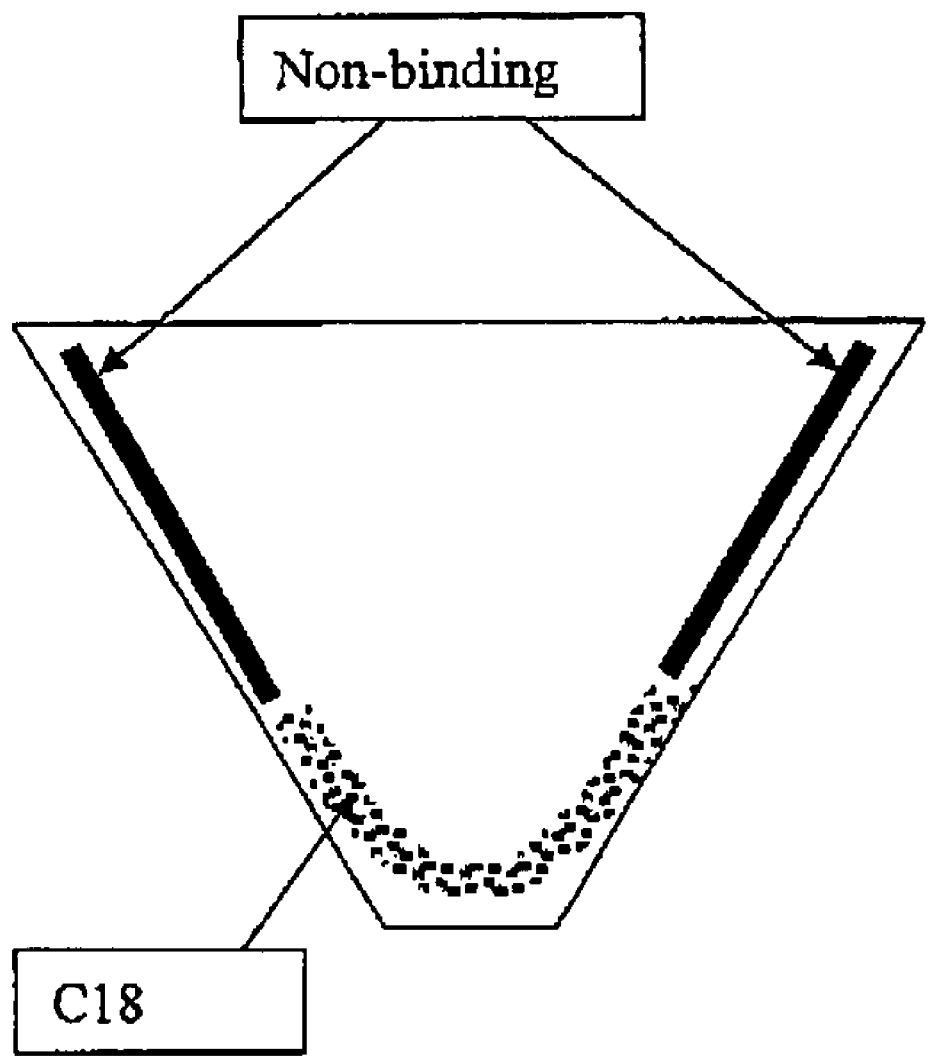
FIG. 5 schematically illustrates a compartment of a solid support having an affinity layer (C18) deposited near the bottom of the compartment and a non-binding surface located near the upper portions of the compartment.

The present invention provides compositions and methods for use in large scale, simultaneous processing of proteins and/or peptides present in a sample such as a cell(s), tissue(s) or biological fluid(s). The subject compositions and methods overcome current limitations in the art by allowing most of the major steps involved in proteomic processing of a sample to be performed at a single location on a solid support or substrate.

In accordance with the present invention, there are provided compositions comprising a solid support or substrate having a plurality of compartments for sample application and processing. At least one compartment has a specific affinity layer attached thereto for protein and/or peptide capture. As used herein "compartment" or "compartments" refers to any separate area or space, which is physically separated by other areas or spaces. Thus, examples of compartments include but are not limited to wells, indentations, chambers, sections, or slots.

Preferably, more than one compartment has a specific affinity layer attached thereto for protein and/or peptide capture. Even more preferably, all or almost all of the compartments have a specific affinity layer attached thereto for protein and/or peptide capture.

The terms "solid substrate" and "solid support" are used interchangeably herein and refer to any apparatus having multiple compartments into which a specific affinity layer may be attached. Thus, a solid support or substrate for use in the present invention may take any number of forms, so long as a specific affinity layer may be attached thereto. As used herein, "plurality" refers to more than one. The term "peptides or proteins" is meant to include all proteinaceous materials including peptides, polypeptides, and full-length proteins as well as fragments and combinations thereof. Hence, the term "peptides or proteins" is used herein in its broadest sense. The term, however, can also refer to a sample comprising proteinaceous material in the form of peptides only, or proteinaceous material in the form of full-length proteins only, or proteinaceous material in the form of fragments of full-length proteins, or any and all combinations thereof.

As described above, in order to reduce the possibility of cross contamination of samples on and/or within the solid support, there should be provided therein or thereon compartments such as separate wells, indentations, chambers, or slots for sample application. Different features may be built into the compartments such as e.g., porous surfaces or rough surfaces to increase surface area and the binding capacity thereof.

The solid support may be any material that is capable of binding or holding the specific affinity layer. For example, glass, plastic, silicones, and elastomers, including silicone, hydrocarbon, and fluorocarbon elastomers may all be used. Ceramic, gold, stainless steel, aluminum, or silicon wafers may also be used as a support. If a metal support is used, the surface thereof may be coated with a material that allows derivatization of the surface. A metal surface may be coated with e.g., silicon oxide, titanium oxide or gold. Preferably, a polymer is used to compose the solid support. Examples of polymers include but are not limited to polypropylene, polystyrene, polyethylene, polymethyl methacrylate, polyvinyl chloride, polymethyl pentene, polycarbonate, polysulfone, polystyrene copolymers such as poly(styrene-co-maleic anhydride) (SMA) and ABS, polypropylene copolymers, cyclic olefin copolymer, fluoropolymers, and polyamides. In a more preferred embodiment, polystyrene is used.

In accordance with the present invention, it has been surprisingly discovered that high quality mass spectrometry (MS) spectra may be obtained for proteins captured on modified polymer surfaces. Thus, polymers, which can be easily and inexpensively manufactured in a wide variety of shapes, are preferred materials for the solid support. Plasma treatment may be used to alter the surface chemistry of polymers. Methods of plasma treatment with inert gases to alter the surface chemistry of polymers are well known and are described in the literature including Sharpe, L. H, and Schonhorn, J., *Adv. Chem. Ser.* (1964) 4:189–201; Hansen, R. H., and Schonhorn, J. (1966)*J. Polym. Sci. B, Polym. Lett. Ed.* 4:203–209; and Sheu, M. S. et al., (1993) *J. Adhesion Sci. Tech.* 7:1065–1076, the disclosures of which are incorporated by reference herein as if full set forth. Plasma coating of polymer microplates as a method is relatively facile, and therefore allows for inexpensive, high-volume manufacture. Preferably, argon plasma treatment is used as described in Examples 1 and 2.

Readily available materials may be used in configuring the solid supports in accordance with the present invention. Examples of materials to which an affinity layer may be applied and which may serve as solid supports include but are not limited to dishes, slides, strips, or plates such as for example, polymer injection molded plates, polymer glass bottom plates, gold deposited plastic plates, microscope slides, microwell plates, microtiter dishes, and microplates. Examples of preferred materials include microwell plates and microtiter dishes.

Examples of specific affinity layers which may be used in the method include but are not limited to hydrophobic surface layers, ionic surface layers, or metal chelating surface layers.

Examples of hydrophobic surface layers for use in the present invention include long chain aliphatic hydrocarbon layers such as e.g., C1 to C18 aliphatic hydrocarbons. Examples of long chain aliphatic hydrocarbons which may be used as specific affinity layers include but are not limited to octadecyl vinyl ether (ODVE), octadecyl amine (ODAM), tri(ethylene glycol)-methyl-vinyl-ether (TMVE), stearyl alcohol (SA), nonylphenoxypoly(ethyleneoxy)ethyl-methacrylate (C9 poly), or stearyloxypolyethyleneoxy-ethylmethacrylate (SPMA).

Examples of ionic surface layers, which may be attached to a solid support, include anionic or cationic surface layers. Examples of anionic surface layers include sulfate anion layers and carboxylate anion layers. Examples of cationic surface layers for use in the present invention include secondary, tertiary, or quaternary amine layers.

An example of a metal chelating surface layer is nickel. Other appropriate metal chelating surfaces include copper, cobalt, zinc, iron, aluminum and calcium.

Multiple samples, each sample comprising a mixture of peptides or proteins, may be applied to a solid support and each sample may be applied to a separate compartment, on or within the solid support. Thus, peptides or proteins present in an individual sample may be captured and adsorbed to an individual compartment having a specific affinity layer attached thereto. This allows simultaneous processing of multiple samples comprising peptides or proteins captured by the specific affinity layer on the solid support. Each sample applied to a compartment may be identified by a numbered ordered arrangement as typically found on microtiter dishes and microwell plates. For example, the solid support may contain an array of horizontal and/or vertical rows of compartments, which form a regular geometric pattern such as a square, rectangle, or circle.

Microwell plates, e.g., those having 96 or 384 wells, are widely used disposable tools for high throughput (HT) drug screening and sample preparation and may be conveniently used in the compositions and methods of the invention. The specific affinity layer may be directly or indirectly deposited preferably to the bottom surface of each individual well, prior to applying the sample comprising peptides or proteins.

As demonstrated schematically in FIG. 1 and FIG. 5, a specific affinity layer may be attached to the bottom and/or inside walls of the wells of a microwell plate which can be used to capture peptides or proteins from a complex mixture. After washing and desalting, the surface captured peptides or proteins can be extracted for MALDI MS analysis.

In one embodiment, the solid support may be a microwell plate. In order to prepare the surface of a hydrophobic C-18 affinity plate, an injection molded microwell plate may be prepared with anhydride-containing copolymers such as poly(styrene-co-maleic anhydride) (SMA). 1-Octadecylamine (ODAM) reacts directly with anhydride copolymers to form a C18 surface. Lee, K. I., (1996) *Styrene-Maleic Anhydride Copolymer. In Polymeric Materials Encycl.* Salamone (ed.), Vol 10, pp. 8010–14.

In another embodiment, glass slides or glass bottom plates may be employed. In order to prepare a glass bottom plate or slide, well-known methods of silane chemistry may be applied to modify the glass bottoms. Polypropylene plates filled with 50% glass spheres may also be modified using such methods. These supports may be modified with an octadecenetrimethoxysilane alcohol solution to form bonded C18 on the plate bottoms or slide surfaces.

In still another embodiment, a gold deposited plate may be used. In order to prepare a gold deposited plate, a C-18 self-assembled monolayer (SAM) surface can be prepared on the gold deposited plate bottom by applying 1-octadecenethiol alcohol solution (ODAM) as described in the examples.

In yet another embodiment, octadecyl vinyl ether (ODVE) may be used as a specific affinity layer on the solid support. ODVE may be dissolved preferably in isopropyl alcohol in a concentration in a range of from about 0.1 to 1.0 weight percent. The ODVE solution may be applied to the solid support, allowed to dry and then exposed to plasma treatment.

One skilled in the art may select different specific affinity layers for use in configuring a solid support based on the ability of the specific affinity layer to capture peptides and proteins. The literature is replete with assays, which may be used to measure levels of protein binding. Such assays include but are not limited to a colloidal gold assay and a fluorescein isothiocyanate-tagged BSA (FITC-BSA) assay. Preferably, an FITC-BSA assay is used.

In accordance with the present invention, it may be desirable to purify dilute samples and concentrate the captured peptides or proteins onto a specific area of a compartment on or within the solid support. Thus in another embodiment, there is provided a solid support for use in performing high throughput analysis of multiple samples, each of said samples comprising a mixture of peptides or proteins, said solid support comprising a plurality of compartments for sample application. One or more compartments has a specific affinity layer attached to a first portion of the compartment and further has a non-binding surface located in a second portion of the same compartment. By "non binding surface" is meant a surface which is low binding for proteins. Such surfaces may be produced following the methods described in U.S. Pat. Nos. 6,093,559 and 6,319,664, the disclosures of which are incorporated by reference herein as if fully set forth. For example, a specific affinity layer may be applied to the bottom surface of one or more compartments, while a non-binding surface may be created on other portions of the same compartment(s) (e.g, the sides or walls of the compartment(s), or the upper sides of walls of the compartment(s)) (FIG. 5). When a dilute protein digest solution is loaded into such a compartment(s), peptides and/or proteins will not only be captured but will also be condensed on the surface having the specific affinity layer attached thereto. After desalting, the captured peptides can be recovered with very small volume of eluant (such as an acetonitrile solution) and loaded onto MALDI MS target plates.

Figure 6:
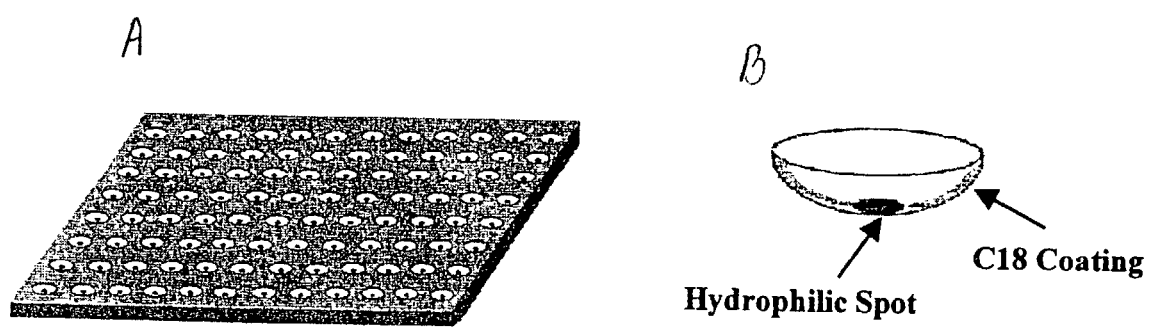
FIGS. 6A and 6B schematically illustrate a microwell plate and a single well of the same microwell plate. The dark oval in the single well represents a hydrophilic spot surrounded by an affinity layer, e.g, C18 (6B). Multiple wells, each having a hydrophilic spot surrounded by an affinity layer are illustrated in the microwell plate (6A).

In another embodiment, the solid support may be configured so that the desalting step and matrix spotting process can be combined, thus reducing the number of transfer steps. The present invention therefore further provides a solid support for use in performing high throughput analysis of multiple samples, each of said samples comprising a mixture of peptides or proteins, said solid support comprising a plurality of compartments for sample application. One or more compartments has a specific affinity layer attached thereto for capture of the peptides or proteins present in the samples and the one or more compartments having a specific affinity layer attached thereto further has a hydrophilic area devoid of and surrounded by the specific affinity layer. For example, after attachment of a specific affinity layer to one or more compartments, a small hydrophilic spot can be created amidst the specific affinity layer by removing a portion of the specific affinity layer using a physical method such as laser ablation (FIG. 6). When a protein digest solution is loaded into such a compartment, peptides will be captured onto the specific affinity layer. After desalting, the captured peptides can be recovered by an eluant or wash solution (e.g., acetonitrile) and then may be co-crystallized with matrix on the hydrophilic area without further transfer to another target plate. This aspect of the invention further reduces loss of sample due to transfer steps.

Of course, the solid support may combine various features described above. For example, one or more compartments having a specific affinity layer attached to a first portion of the compartment(s) may further have a hydrophilic area devoid of and surrounded by the specific affinity layer. The same compartment or compartments may also have a non-binding surface located in a second portion thereof.

In another aspect of the invention, there is provided a method for performing high throughput analysis of multiple samples, each of said samples comprising a mixture of peptides or proteins. In accordance with the method, individual samples may be simultaneously processed at different locations (compartments) on the solid support. The method comprises the steps of: (1) providing a solid support with a plurality of separate compartments for sample application, wherein one or more of the compartments has a specific affinity layer attached thereto for capture of the peptides or proteins present in the sample; (2) applying a sample or an aliquot thereof to a separate compartment having a specific affinity layer attached thereto; (3) washing the peptides or proteins which have been captured by the specific affinity layer, and (4) performing high throughput electrospray ionization (ESI) or matrix-assisted laser desorption/ionization mass spectrometry (HT MALDI MS) analysis on the captured peptides or proteins. Preferably, high throughput matrix-assisted laser desorption/ionization time of flight mass spectrometry (HT MALDI TOF MS) analysis is performed.

In a further embodiment, the method comprises the steps of: (1) providing a solid support with a plurality of compartments for sample application, one or more of said compartments having a specific affinity layer attached thereto for capture of the peptides or proteins in the sample, wherein the one or more compartments having a specific affinity layer attached thereto has the layer attached to a first portion of the one or more compartments and further has a non-binding surface located on a second portion of the same compartment(s); (2) applying each of said samples or an aliquot thereof to a separate compartment having the specific affinity layer attached thereto; (3) washing the peptides or proteins which have been captured by the specific affinity layer on the solid support, and (4) performing high throughput electrospray ionization (ESI) or matrix-assisted laser desorption/ionization mass spectrometry (HT MALDI MS) analysis on the captured peptides or proteins. Preferably, high throughput matrix-assisted laser desorption/ionization time of flight mass spectrometry (HT MALDI TOF MS) analysis is performed.

In still another aspect of the invention, there is provided a method for performing high throughput analysis of multiple samples, each of said samples comprising a mixture of peptides or proteins. The method comprises the steps of: (1) providing a solid support with a plurality of compartments for sample application, wherein one or more of the compartments has a specific affinity layer attached thereto for capture of the peptides or proteins present in the samples and wherein the one or more compartments having a specific affinity layer attached thereto further comprises a hydrophilic area devoid of and surrounded by the specific affinity layer, (2) applying a sample or an aliquot thereof to the one or more compartments having a specific affinity layer attached thereto, (3) washing the peptides or proteins which have been captured by the specific affinity layer on the solid support, and (4) performing high throughput electrospray ionization (ESI) or matrix-assisted laser desorption/ionization mass spectrometry (HT MALDI MS) analysis on the captured peptides or proteins. Preferably, high throughput matrix-assisted laser desorption/ionization time of flight mass spectrometry (HT MALDI TOF MS) analysis is performed.

In yet a further embodiment, a method is provided for performing high throughput analysis of multiple samples, wherein each of the samples comprises a mixture of peptides or proteins. The method comprises the steps of: (1) providing a solid support with a plurality of separate compartments for sample application, wherein one or more of the compartments has a specific affinity layer attached thereto for capture of the peptides or proteins present in the sample, wherein the specific affinity layer is attached to a first portion of the one or more compartments, wherein the first portion of the one or more compartments comprises a hydrophilic area devoid of and surrounded by the specific layer attached thereto and wherein the one or more compartments further comprises a non-binding surface located in a second portion thereof, (2) applying a sample or an aliquot thereof to a separate compartment having a specific affinity layer attached thereto; (3) washing the peptides or proteins which have been captured by the specific affinity layer, and (4) performing high throughput electrospray ionization (ESI) or matrix-assisted laser desorption/ionization mass spectrometry (HT MALDI MS) analysis on the captured peptides or proteins. Preferably, high throughput matrix-assisted laser desorption/ionization time of flight mass spectrometry (HT MALDI TOF MS) analysis is performed.

In any of the subject solid support compositions or methods using the solid support compositions for performing high throughput analysis of multiple samples, it is preferable that more than one compartment has a specific affinity layer attached thereto for protein and/or peptide capture. Even more preferably, all or almost all of the compartments have a specific affinity layer attached thereto for protein and/or peptide capture.

In accordance with the methods of the present invention, either an entire sample is applied or an aliquot of the sample is applied. The term "aliquot" as used herein means a portion of a sample but can include the entire sample in some instances especially if the sample size is small. Typically, aliquots having anywhere from about a few atom moles to about 100 picomoles of proteinaceous material in a volume of from about 1 µl to about 500 µl are applied to a single location (compartment) on the specific affinity layer of the solid support. The sample is contacted to the specific affinity layer for a period of time sufficient to allow the peptides or proteins to bind to the specific affinity layer. Typically, a sample is contacted with the specific affinity layer for a period of time in the range of from about 30 seconds to about 12 hours. Preferably, the sample is contacted with the specific affinity layer for a period of time in the range of from about 30 seconds to about 15 minutes.

Many different eluants or wash solutions may be used in the subject methods to remove unbound, non-proteinaceous material. For instance, pH-based eluants, which modify the selectivity of the specific affinity layer based upon pH (charge), may be used and include known pH buffers, acidic solutions and basic solutions. Wash solutions that modify the selectivity of the specific affinity layer may also include ionic strength-based eluants such as salt solutions of different types and concentrations. Eluants, which modify the selectivity of the specific affinity layer with respect to surface tension and protein or peptide structure, include detergents and surfactants such as e.g., CHAPS, TWEEN, and NP-40. Eluants, which modify the selectivity of the specific affinity layer based on hydrophobic interaction, include urea, organic solvents such as propanol, acetonitrile, ethylene glycol and glycerol, and detergents.

Based on different parameters such as source of the peptide or protein sample, and type of specific affinity layer attached to the solid support, one skilled in the art of chemical or biochemical analysis is capable of determining the optimal wash conditions. For example, washes especially suited for use on hydrophobic surface layers include urea, organic solvents and detergents. Eluants useful for washing peptides or proteins captured by ionic surface layers include dilute aqueous buffers. Eluants useful for washing peptides or proteins captured by metal chelating surfaces include metal chelating surfaces including, but not limited to imidazole buffers, low pH or TRIS or other buffer including salts, e.g., sodium chloride and imidazole. Typically, the eluant is contacted to the specific affinity layer on the solid support at a temperature in the range of from about 0° to 100° C. Preferably, a wash temperature in the range of from about 4° to about 37° C. is used.

After washing the captured peptides or proteins, if MALDI MS is the analytical tool of choice, the peptides or proteins are ultimately contained in a photo-excitable matrix. Examples of matrices which may be used in the methods of the invention include but are not limited to dihydroxybenzoic acid (dhb) in acetonitrile, nicotinic acid, sinapinic acid, succinic acid, glycerol, alpha-cyano-4-hydroxycinnamic acid (HCCA), alpha-cyano-4-hydroxycinnamic-acid-methyl-ester (a-CNME), 2,3,4-trihydroxyacetophenone (2,3,4-THAP), 2,4,6-trihydroxyacetophenone (2,4,6-THAP) and 3-hydroxypicolinic acid.

Conventional MALDI-MS equipment and methods may be applied. Commercial systems are available such as e.g., HP 62025A MALDI-TOF (Hewlett-Packard Co., Palo Alto), PerSpective Biosystem Elite TOF, (PerSeptive Biosystems, Framingham, Mass.) and IonSpec Ultima FT Mass Spectrometer (IonSpec, Irvine Calif.).

The invention is further illustrated by the following specific examples, which are not intended in any way to limit the scope of the invention.

EXAMPLE 1

Preparation of Octadecyl Vinyl Ether Coated Microwell Plates and Optimization of the Coating Process Among the five compounds screened, octadecyl vinyl ether (ODVE) coated plate (0.2%) showed highest protein capture tested by colloidal gold. Therefore ODVE was chosen for further testing by the FITC-BSA assay as the most successful surface, especially ODVE coated on non-treated polystyrene. FIG. 2A reports the result of protein capture on untreated polystyrene surface.

ODVE was used as purchased from Aldrich Chemicals. The ODVE was dissolved in isopropanol at a concentration range 0.1 to 1 weight %. The microplates were either Corning 384 well or Corning half-volume 96 well plates tissue culture-treated polystyrene (TC). Coating was achieved by addition of the coating solution to microplate wells followed by argon plasma treatment. The coating solution was added to wells ~100 µl, and removed after approximately 1 hr, dried for approximately 10 min. at 40° C. and then exposed to argon plasma in a Plasmod Etcher (MPS 300 RF Power Module with GCM-250 gas control module, March Instrument Inc.). The argon plasma was generated using argon at approximately 12 psi and in a vacuum of 0.8–1.0 torr. The treatment time range was 10 to 300 s at a RF power of 25 W.

To determine the optimal plasma exposure time, 1%, 0.5%, and 0.2% ODVE solutions were coated onto non-treated polystyrene plates (96 well, half-volume). 100 µl of coating solution was added per well. Argon plasma exposure time was varied between 10 and 300 s. Coated plates were then tested for protein capture and recovery using fluorescent-labeled BSA assay. 1 mg/ml fluorescein isothiocyanate-tagged BSA (FITC-BSA) in 0.1% TFA/H$_2$O was added to coated microplate wells and left overnight. This solution was then removed and wells were washed twice with 0.1% TFA/H$_2$O. 70% acetonitrile was then added to selected wells (100 µl) to elute the bound protein. This solution was agitated by up and down pipetting and then removed. Wells were again washed twice with 0.1% TFA/H$_2$ 0.1M Borate buffer was then added to the wells and fluorescence was measured 30 min. later using a plate reader set to an excitation wavelength of 492 nm and an emission wavelength of 535 nm. Fluorescence of capture wells (no acetonitrile addition) was compared to that of capture and recovery wells (acetonitrile addition) for each coating concentration and at each plasma exposure time (FIG. 2B). All measurements were taken using a Perkin Elmer plate reader.

EXAMPLE 2

ODVE Coated Microwell Plates for MALDI TOF MS Analysis

To evaluate the utility of the C18-coated microwell plates, bovine serum albumin (BSA) was digested with trypsin in a 100 mM NH$_4$HCO$_3$ solution (1 mg/ml) overnight at 37° C. The BSA digest was diluted to desired concentration in 100 mM NH$_4$HCO$_3$. The tryptic digest was adsorbed by placing 1–2 µl of the digest into a well of the coated plate, and allowing the sample to be air-dried. Each well in the plate was washed twice with 10 µl 0.1% TFA solution to desalt the peptides followed by 2 µl of 50–75% acetonitrile water solution to extract the captured peptides. The MALDI TOF MS analysis consists of placing 1–2 µl of the peptide solution in acetonitrile onto a stainless steel target plate and adding about 1 µl of matrix solution on target. The matrix used was α-cyano-4-hydroxycinnamic acid (HCCA) obtained from Aldrich. HCCA was dissolved in 70% acetonitrile at a concentration of approximately ~10 mg/ml. Mass spectra were acquired on the Bruker MALDI TOF BiflexIII instrument. Good MALDI TOF mass spectra were obtained after purification of C18 coated plates as showed in the FIGS. 3A–C.

EXAMPLE 3

C18 on Gold Coated Microwell Plates

Gold was sputtered onto 384 polystyrene half-volume microplates. The plates were coated with a solution of 1-octadecenethiol (ODAM) in alcohol to create a self-assembled monolayer (SAM) surface that can capture proteins and peptides. Each well was loaded with ~17 µl 1-octadecanethiol alcohol solution (1 mM), after 30 minutes the plate were washed three times with alcohol, and air-dried. The tryptic BSA digest was used to evaluate the C18 coated plate using the method mentioned in example 2. The tryptic digest of BSA purified on the 1-octadecenethiol coated plated gave a MALDI mass spectral data comparable to ODVE coated plate (FIGS. 4A–F).

Although the present invention has been described generally and in detail by way of examples, persons skilled in the art will understand that the invention is not limited to the embodiments specifically disclosed, and that modifications and variations can be made without departing from the spirit and scope of the invention. Therefore, unless changes otherwise depart from the scope of the invention as defined by the following claims, they should be construed as included herein.

REFERENCES

The following references and those cited throughout the specification are incorporated herein by reference.

1. Naaby-Hansen, S: Waterfoe;d, M. D.; Cramer, R. Trends in Pharmacological Sciences, 2001, 22, 376–384.

2. Anderson, L.: Seilhamber, J. Electrophoresis 1997, 18, 533–537.
3. Gygi, S. P. et al As a matter of law. Cell. Biol. 1999, 19, 1720–1730.
4. Dove, A. Nature Biotechnology, 1999, 17 233–236.
5. Edwards, A. M.: Arrowsmith, C. H.: Pallieres, B. Modern Drug Discovery, 2000, 5(7), 35–44.
6. Nature, 1999, 402, 715–719.
7. Lee, K. H. Trends in Biotechnology, 2001, 19, 217–222.
8. Fenn, J. B.: Mann, M.: Menig, C. K.; Wong, S. F.; Whitehouse, C. M. Science, 1989, 246, 64.
9. Cole, R. B.; Electrospray Ionization Mass Spectrometry: Fundamentals, Instrumentation and Applications; Wiley: New York, 1997.
10. Karas, M.; Hillenkam, F. Anal. Chem. 1995, 60, 2299.
11. Loo, J. A. Bioconjugate Chem. 1995, 6, 644.
12. Barber, M.; Mordoli, S. R.; Sedgwick, R., A. N. J. Chem. Soc. Commun., 1981, 325.
13. Aebersold, R.; Goodlett, D. R. Chem. Review. 2001, 101, 269–295.
14. Chaurand, P.; Luetzenkirchen, F.; Spengler, B. J. Am. Soc. Mas. Spectrom. 1999, 10, 91.
15. Loo, J. A.; Edmonds, C. G.; Smith, R. D. Anal. Chem 1993, 65, 425–438.
16. Langen, H.; Takacs, B.; Evers, S.; Bermdt, P.; Lahm, H. W.; Wipf, B.; Gray, C.; Fountoulakis, M. Electrophoresis 2000, 21, 411.
17. Naaby-Hansen, S; Waterford, M. D.; Cramer, R. Trends in Pharmacological Sciences, 2001, 22, 376–384.
18. Pluskal, M. G. Nature Biotechnology 2000, 18, 104–105.
19. Watten, M. E.; Brockman, A. H.; Orlando, R. Anal. Chem. 1998, 70, 3757–3761.
20. Beavis, R. C.; Chait, B. T.; Methods Enzymols. 1996, 270, 519–551.
21. Wang, M. Z.; Fitzgerald, M. C. Anal. Chem. 2001, 73, 625–631.
22. Zhang, N.; Doucette, A., Liability, L. Anal. Chem. 2001, 73, 2968–2975.
23. Doucette, A.; Craft, D.; Liability, L. Anal. Chem. 2000, 72, 3355–3362.
24. Warren, M. E.; Brockman A. H.; Orlando, R. Anal. Chem. 1998, 70, 3757–3761.
25. Schurengerg, M. et al. Prestructured MALDI Sample Supports: Sample Washing and Recrystallization, Bruker Daltonics; Bremen, 2001.
26. Sharpe, L. H.; Schonhorn, J. Adv. Chem. Ser. 1964, 4, 189–201.
27. Hansen, R. H.; Schonhorn, J. J. Polym. Sci. B, Plym. Lett. Ed. 1966, 4, 203–209.
28. Sheu, M. S. et al. J. Adhesion Sci. Technol. 1993, 7, 1065–1076.
29. Davies, J. et al. Colloids and Surfaces A: Physicochem. Eng. Aspects 2000, 174, 287–295.

We claim:

1. A solid support for use in performing high throughput analysis of multiple samples, each of said samples comprising a mixture of peptides or proteins, said solid support comprising a plurality of wells having side walls and a bottom surface; said side walls of each said well have a specific affinity layer attached thereto; wherein said specific affinity layer for capture of said peptides or proteins present in the samples is at least one of a hydrophobic surface layer, an ionic surface layer, or a metal chelating surface layer.

2. The solid support of claim 1 which is comprised of a polymer.

3. The solid support of claim 2 wherein the polymer is at least one of polypropylene, polystyrene, polyethylene, polymethyl methacrylate, polyvinyl chloride, polymethyl pentene, polycarbonate, polysulfone, polystyrene copolymer, polypropylene copolymer, cyclic olefin copolymer, fluoropolymer, poly(styrene-co-maleic anhydride) or polyamide.

4. The solid support of claim 1 comprising a microwell plate or microtiter dish.

5. The solid support of claim 1 wherein the hydrophobic surface layer is a long chain aliphatic hydrocarbon including at least one of octadecyl vinyl ether (ODVE), octadecyl amine (ODAM), tri(ethylene glycol)-methyl-vinyl-ether (TMVE), stearyl alcohol (SA), nonylphenoxypoly(ethyleneoxy)-ethyl-methacrylate (C9 poly), or stearyloxypolyethyleneoxy-ethyl-methacrylate (SPMA).

6. The solid support of claim 1 wherein the specific affinity layer is attached to said bottom of said well, wherein said bottom further comprises a hydrophilic area devoid of and surrounded by the specific affinity layer attached thereto and wherein said sidewall of said well further comprises a non-binding surface located on the upper portion thereof.

* * * * *

UNITED STATES PATENT AND TRADEMARK OFFICE
CERTIFICATE OF CORRECTION

| | | |
|---|---|---|
| PATENT NO. | : 7,214,353 B2 | Page 1 of 1 |
| APPLICATION NO. | : 10/232346 | |
| DATED | : May 8, 2007 | |
| INVENTOR(S) | : Bernice Ida Feuer et al. | |

It is certified that error appears in the above-identified patent and that said Letters Patent is hereby corrected as shown below:

On The Title Page, Item (74) should read --*Attorney, Agent, or Firm* – Thomas R. Beall; Vincent T. Kung; Tina N. Thompson-- not "*Attorney, Agent, or Firm* – Thomas R. Beali; Vincent T. Kung; Tina N. Thompson"

Signed and Sealed this

Twenty-third Day of October, 2007

JON W. DUDAS
*Director of the United States Patent and Trademark Office*